United States Patent [19]
Lin et al.

[11] Patent Number: 5,635,980
[45] Date of Patent: Jun. 3, 1997

[54] SYSTEM AND METHOD FOR CUSTOMER PREMISES BROADBAND INTERFACE WITH ON-HOOK ALERTING

[75] Inventors: Steve M.-C. Lin, East Brunswick; Frederick C. Link, Red Bank; Barry K. Schwartz, Stockton, all of N.J.

[73] Assignee: Bell Communications Research, Inc., Morristown, N.J.

[21] Appl. No.: 416,418

[22] Filed: Apr. 4, 1995

[51] Int. Cl.⁶ .......................... H04N 7/14; H04M 11/00
[52] U.S. Cl. .................... 348/13; 348/6; 348/14; 379/90; 379/93; 379/96
[58] Field of Search .................... 348/13, 6, 7, 17, 348/14, 16, 8, 10, 12; 379/90, 94, 96, 97, 98, 399

[56] References Cited

U.S. PATENT DOCUMENTS

| | | | |
|---|---|---|---|
| 5,014,125 | 5/1991 | Pocock et al. | 348/7 |
| 5,394,461 | 2/1995 | Garland | 379/106 |
| 5,416,831 | 5/1995 | Chewning, III et al. | 379/97 |

*Primary Examiner*—Curtis Kuntz
*Assistant Examiner*—Stephen Palan
*Attorney, Agent, or Firm*—Joseph Giordano

[57] ABSTRACT

A broadband customer premises equipment ("CPE") interface device interfaces with conventional telephones, screen phones, and broadband data and video devices. The interface device includes circuitry to connect with a telephone network via a first telephone connection and circuitry to connect with a broadband network via a second, broadband connection. The interface device can provide control of video information being pumped to the CPE via the broadband network by sending control signals to a video server via the telephone network. In addition, the interface device includes ADSI off-hook alerting ("AOHA") circuitry and adds ADSI script management server ("ASMS") circuitry to provide noninvasive programming of screen phone-type CPE devices. ASMS programming information for a CPE device is transferred to the interface device via the broadband network and stored in the interface device. The AOHA and ASMS circuitry requests the CPE device to go off-hook when idle, without ringing the CPE device like a conventional telephone call. When the CPE is idle, the AOHA and ASMS circuitry routes the programming information from storage into the CPE.

7 Claims, 2 Drawing Sheets

SYSTEM AND METHOD FOR CUSTOMER PREMISES BROADBAND INTERFACE WITH ON-HOOK ALERTING

BACKGROUND OF THE INVENTION

The present invention relates generally to the field of customer premises equipment ("CPE") for telephone networks, and more specifically to CPE devices capable of interfacing with both telephone and broadband networks.

CPE devices for use in today's telephone network are becoming more intelligent all the time. Today, screen phone-type CPEs permit sophisticated customer services through the telephone network. For example, screen phone-type CPEs interface with today's telephone network elements and other computers to transmit and receive voice and data according to the Analog Display Services Interface ("ADSI") standard. ADSI is an industry standard written by Bellcore, the assignee of the present application. These CPEs, also referred to as "smart phones," receive data and programming information via the telephone network to expand telephone services.

Service providers wishing to modify programming information or send other information to customers prefer to do so during off hours, when telephone traffic is at a minimum and costs are lower. Because CPEs operate with the telephone network, however, to interface with a CPE, a computer or network element must call the CPE in accordance with conventional call processing protocols. Thus, the CPE will ring in response to this call, disturbing the customer. There is some movement toward changing the telephone network elements to allow for an inaudible alert to CPE devices, but those changes are very expensive and years away.

At the same time new CPE devices are being developed, new network elements and services are also being developed. For example, today there exists a big emphasis on developing broadband networks for feeding video information to customers' homes. These broadband networks include, for example, digital asynchronous transfer mode ("ATM") switches to route large amounts of digital information quickly and efficiently. Broadband networks provide yet another source of information for customers and customer services including, for example, video programs on demand and other forms of interactive TV, High Definition Television ("HDTV"), graphics databases, multimedia data, and data to and from very high speed supercomputers. Therefore, significant benefits can be derived from CPE devices that interface with broadband network elements, as well as today's existing telephone network elements.

Accordingly, it is desirable to provide a CPE system and method capable of interfacing with broadband networks as well as today's telephone networks.

Additional desires of the invention will be set forth in the description which follows, and in part will be apparent from the description or may be learned by practice of the invention. The advantages of the invention may be realized and obtained by means of the instrumentalities and combinations particularly pointed out in the appended claims.

DISCLOSURE OF THE INVENTION

To achieve the foregoing desires and objects, and in accordance with the purposes of the invention as embodied and broadly described herein, the present invention provides an interface device for customer premises equipment, wherein said customer premises equipment includes a screen-phone device, comprising first channel means for communicating telephony information to and from a telephone network; second channel means, separate from the first channel means, for communicating broadband information to and from a broadband network; means for routing said telephony information to said customer premises equipment connected to said interface device; and routing control means for routing certain broadband information to said customer premises equipment in response to predetermined signals from said broadband network.

BRIEF DESCRIPTION OF THE DRAWINGS

The accompanying drawings, which are incorporated in and constitute a part of the specification, illustrate presently preferred implementations of this invention and, together with the general description given above and the detailed description of the preferred implementations given below, serve to explain the principles of the invention.

In the drawings.

BEST MODE FOR CARRYING OUT THE INVENTION

Reference will now be made in detail to the construction and operation of preferred implementations of the present invention which are illustrated in the accompanying drawings.

The following description of the preferred implementations of the present invention is only exemplary of the invention. The present invention is not limited to these implementations, but may be realized by other implementations.

Figure 1:
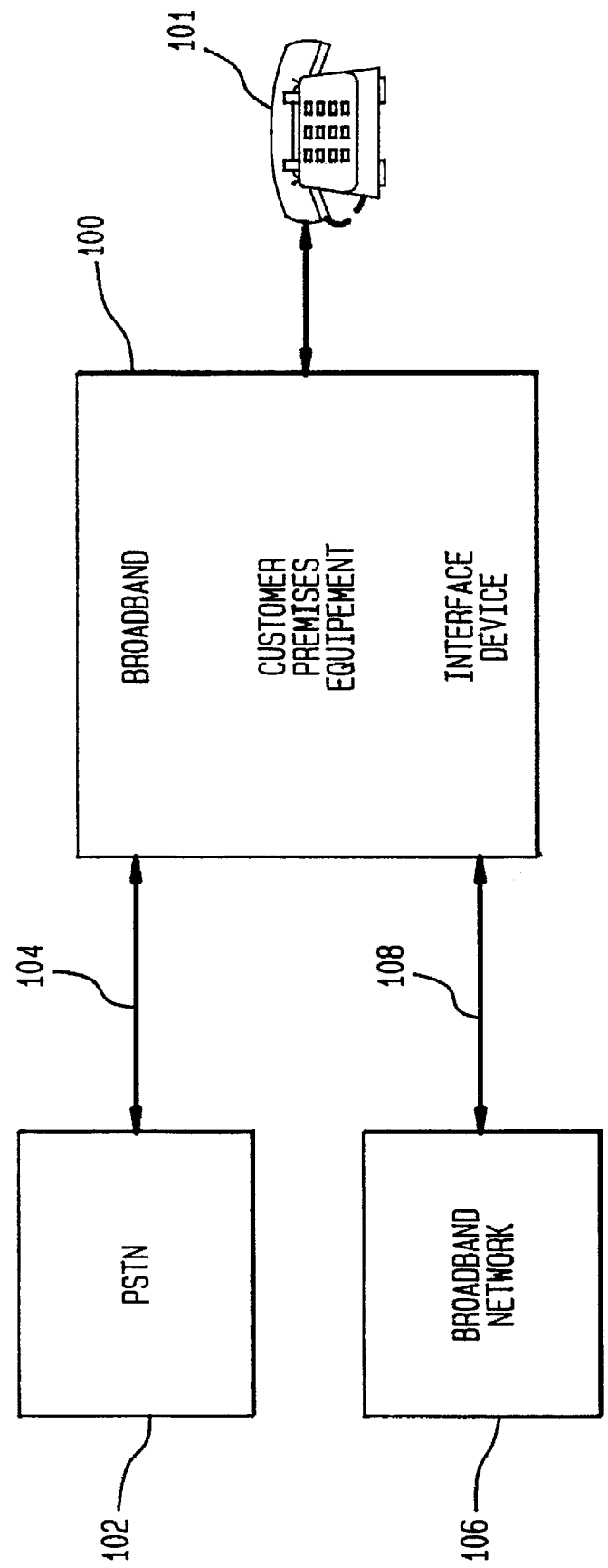
FIG. 1 is a block diagram of a combined telephone/broadband network configuration using a CPE device in accordance with one embodiment of the invention.

FIG. 1 shows a block diagram of a combined telephone/broadband network configuration using a broadband CPE interface device ("BCID") 100 in accordance with a preferred embodiment of the present invention. BCID 100 provides an interface between end user device 101, e.g., telephones, TVs, computers, and the Public Switched Telephone Network ("PSTN") 102 and a broadband network 106. BCID 100 preferably connects to the PSTN 102 via a standard analog telephone line 104 and connects to the broadband network 106 via a broadband access loop 108.

Broadband access loop 108 may comprise, for example, a fiber or coaxial cable loop, or some other means capable of handling broadband digital transmission signals from the broadband network. Other possible means include, depending on the bandwidth needed for the supported applications, Asynchronous Digital Subscriber Lines ("ADSL"), Broadband Integrated Services Digital Network ("B-ISDN") access lines, radio based access, and interactive cable Television ("TV") channels.

Figure 2:
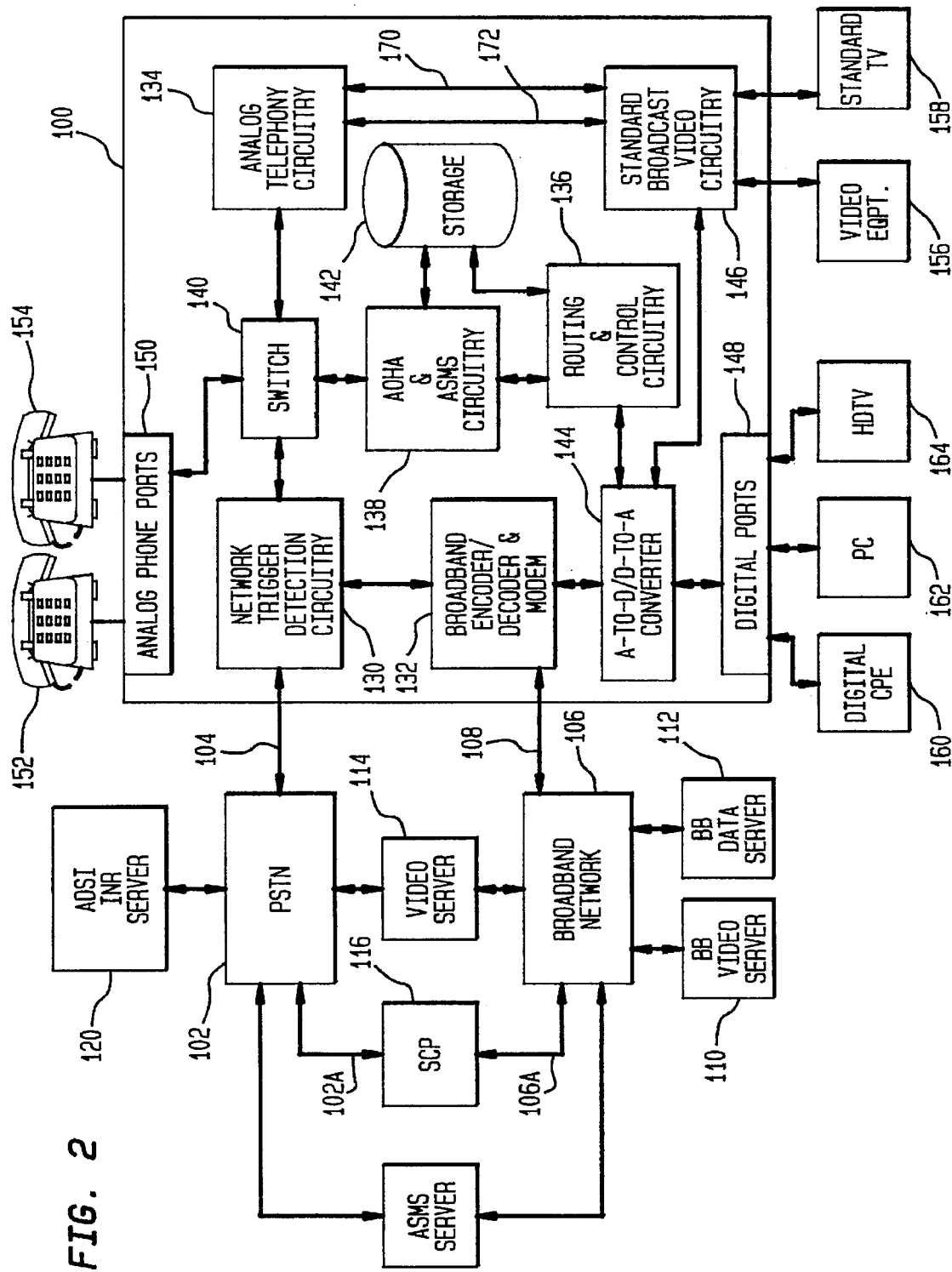
FIG. 2 is a detailed block diagram of a broadband CPE interface device in accordance with one embodiment of the present invention.

FIG. 2 shows a more detailed drawing of the BCID and network configuration according to a preferred embodiment of the invention.

The BCID 100 provides access to high speed digital data, video, and high definition television applications. Broadband network 106 receives and forwards this type of information from a variety of sources including broadband video server 110, broadband data server 112, and intelligent network elements such as service control points ("SCP"s) 116. Broadband video server 110 may comprise, for example, a library of video information, such as movies or other programs. Broadband data server 112 may comprise any source of high speed or high density data, such as graphics including multimedia combinations with text and digitized audio. Video server 114 interfaces with both the PSTN 102 and broadband networks 106 and may communicate data and control signals to and from the BCID 100 via the PSTN 102 while communicating video or other broadband information to the BCID 100 via the broadband network 106. PSTN 102 is preferably connected to a SCP 116 via SS7 connections 102A. Broadband network 106 is preferably connected to a SCP 116 via control channels within the SCP connection 106A with the broadband network 106. SCP 116 supplies certain call processing and network supplemental service information to the PSTN 102 or broadband network 106 from internal or external databases.

The PSTN 102 also connects to a standard ADSI and/or interactive voice response ("IVR") server 120. The ADSI functions of the ADSI and IVR server 120 provide conventional interactive data for smart phone-type CPEs 154 connected to the BCID 100. The IVR functions of the ADSI and/or IVR server 120 provide conventional interactive voice prompts to smart phone-type CPEs 154 and to standard phone-type CPEs 152 connected to the BCID 100.

The PSTN 102 and broadband network 106 also connect to a conventional ADSI script management server ("ASMS") 118. ASMS 118 stores programming information for smart phone-type CPEs 154 in accordance with conventional techniques such as those published for ADSI script management by Bellcore. Normally, ASMS scripts would be delivered to a smart phone-type CPE 154 via the PSTN 102. However, in accordance with the present invention, as described in more detail below, ASMS scripts can be delivered to a smart phone-type CPE 154 via the BCID 100 and broadband network 106.

In accordance with the present invention, BCID 100 preferably includes network trigger detection circuitry 130, broadband encoder/decoder and modem 132, analog telephony circuitry 134, routing and control circuitry 136, which may be software controlled and which can control the selection and function of the other BCID components (not all control connections shown) in response to user inputs. BCID also includes ADSI On-Hook Alerting ("AOHA") and ASMS circuitry 138, switch 140, storage 142, A-to-D and D-to-A converter 144, standard and broadcast television video circuitry 146, digital ports 148, and analog phone port 150.

BCID 100 preferably connects to conventional analog telephones 152 and/or screen phone-type or smart phone-type CPEs 154 via analog phone ports 150 and to digital CPEs 160, PCs 162, and/or high definition television ("HDTV") 164 via digital ports 148. NTSC video circuitry 146 connects to and provides information to external video equipment such as Video Cassette Recorders ("VCRs") 156 and standard TV 158.

BCID 100 may be mounted on the outside wall of a customer's premises provided protection (not shown) is included against lightning, short circuits with adjacent power lines, wind damage, rain damage, and other exterior hazards. Alternatively, BCID 100 may be mounted inside a customer's premises, where, for example, a digital loop carrier, or other telephone line wiring, 104 enter the premises, or in a television set top box, resembling those provided in many cable TV home installations today. The functions of the proposed equipment do not depend on the exact mounting point or configuration.

Within broadband CPE 100, the broadband network access loop 108 preferably terminates on broadband encoder/decoder and modem 132. Broadband encoder/decoder and modem 132 may include digital decoding and encoding circuitry or analog transmission and reception circuitry with suitable modem functions. Broadband encoder/decoder and modem 132 receives incoming broadband information, decodes or demodulates the information, and/or routes the information to A-to-D/D-to-A converter 144.

Storage 142 preferably stores digital data for speed conversion (data buffering) to data rates compatible with the device to which the data is being routed, as well as for temporary storage of downloaded data for delayed delivery to equipment at a later time. Storage 142 may also temporarily hold feature script logic and associated data intended to automatically update programs that run on a screen-based CPE 154. For example, as described in more detail below, BCID 100 can preferably be used to inexpensively and rapidly download CPE resident feature program scripts and associated data, along with control and routing information from ASMS 118 into storage 142 via broadband network 106. The control and routing information may contain information indicating which CPEs 154 are intended to receive the corresponding program scripts and whether an automatic update should be delivered to an idle CPE 154 inaudibly or accompanied by an audible alert signal.

More specifically, when a smart phone-type CPE 154 owner initially calls into an ASMS 118 to subscribe to ASMS services, a certain I.D. code associated with that CPE 154 is stored at the ASMS 118. Without the BCID 100 of the present invention, the ASMS 118 would call the customer premises of the desired smart phone 154 over the PSTN 102. The PSTN, which would have to be extensively modified for the task, would transmit a special code, called here the AOHA code, along with the I.D. code of the associated smart phone and a program or data update from the ASMS. This information cannot be sent to the associated smart phone without an obtrusive ringing signal. The BCID 100 and broadband network 108 of the present invention can be used to provide an improved smart phone 154 update from an ASMS 118 as follows.

In accordance with the present invention, any programming updates for that CPE 154 are preceded by the I.D. code, then sent to the BCID 100 via broadband network 106. To update a smart phone-type CPE 154, ASMS 118 sends an AOHA code and the I.D. code to instruct a particular CPE 154 connected to the BCID 100 to go off-hook to receive programming information. The AOHA code itself, provides a nonobtrusive alert code to the CPE 154 which does not require the CPE 154 to ring like a conventional telephone call.

The proposed BCID 100, to support this CPE update, decodes the received information at the broadband encoder/decoder modem 132, and, upon identifying the received information as a CPE program update download, downloads particular application information into storage 142. Then, after AOHA and ASMS circuitry 138 tests the CPE 154 for an idle condition, BCID 100 downloads the updated scripts and/or data to the target CPE 154 when the phone tests idle. For ADSI compatible smart phone-type CPEs 154, the BCID 100 preferably uses the AOHA capability and Feature Download protocol as described, e.g. in Bellcore's Family of Requirements document FR-12, 1993 ed.

The BCID 100, according to the present invention, also provides other broadband and voiceband interaction functions. For example, in a preferred embodiment, BCID 100 permits analog telephony functionality to control broadband functionality, such that outgoing transmissions can be routed through the appropriate, user selected, broadband network carriers to a desired destination. In addition, BCID 100 can send data and control commands to a PSTN Advanced Intelligent Network ("AIN") node, such as SCP 116, via broadband network 106, to control the execution of special call processing functions that are not normally available in or from AIN compatible switching systems of the PSTN.

An example of a broadband-based service that can be implemented using a BCID 100 according to the present invention is carrier select service. For carrier select service, a user's screen-based CPE 154 might display a list of PSTN local and interexchange carriers at a given time of day and their latest price per minute for a carried call. A user wishing to make a PSTN call could choose to override his or her presubscribed carrier with one offering a better price for that call. The user would select the carrier desired, then dial the called directory number in the usual way. The analog telephony circuitry 134 is preferably programmed to generate the dialable called number, including carrier identification codes, in the proper sequence, and to outpulse these to the PSTN 102 via DTMF signals.

Alternatively, this carrier select service is provided where a service reached over the PSTN displays a list of broadband carriers by time of day and by price to the user. When the user selects the desired carrier, and provides the broadband destination address of a desired service, the full broadband network destination address is then formulated and is transmitted by the proposed CPE to cause the broadband network to route the CPE to the service provider over the desired carriers. The PSTN service can then be disconnected by the user, or automatically by the CPE programming.

Referring again to FIG. 2, the PSTN analog loop 104 enters the BCID 100 and connects to Network Trigger Detection Circuitry ("NTDC") 130. Switch 140 connects the NTDC 130 and analog telephony circuitry 134 to the locally connected analog telephones 152 and 154. During normal operation, switch 140 connects the PSTN analog loop 104 to its analog telephony circuitry to process PSTN calls in a conventional manner. However, upon command from the BCID 100, switch 140 disconnects the analog telephony circuitry from the NTDC. In this way ADSI compatible screen-based CPEs 154 can receive automatic feature downloads from the AOHA and ASMS circuitry 138. Again, as described above, the information being downloaded by the AOHA and ASMS circuitry 138 was preferably previously received over broadband network 106 from ASMS server and temporarily held in storage 142 until the CPE 154 becomes idle. Since an ADSI CPE 154 must be taken off-hook to receive a CPE-resident feature script or data update, the analog PSTN loop 104 must be disconnected from the local analog telephony circuitry 134. If the PSTN loop 104 were not disconnected, then the off-hook ADSI CPE 154 would be interpreted by the serving PSTN switching system as a request to make a telephone call, when the ADSI phone is, instead, off-hook to receive a feature update.

To support the off-hook state of an ADSI CPE 154, AOHA and ASMS 138 preferably provides standard PSTN off-hook supervision based on direct current detection over the local analog transmission path at the customer premises. Should a Dual-Tone MultiFrequency ("DTMF") signal, a disconnect signal, or a flash signal (all as defined for the PSTN) be detected during the download, the AOHA and ASMS circuitry 138 preferably ceases transmitting the download information over the analog phone ports 150 and connects the path to the PSTN loop 104 via switch 140 to provide dial tone to the customer. This BCID functionality provides a rapid abort of an automatic download operation to an ADSI CPE 154 when a user needs to make a PSTN telephone call and can't wait for completion of the download.

NTDC 130 preferably includes an AIN CPE network integrator as described, for example, in U.S. patent application Ser. No. 08/204,106, assigned to Bellcore, the contents of which is incorporated by reference.

Analog telephony circuitry 134 preferably provides conventional telephone and visual display, user keypad, soft keys, and keyboard functionality of an internal screen phone in the same manner as those of the external phones 152 and CPEs 154. Alternatively, display information included in an ADSI call may be carried over access video channel 170 to an analog or digital TV 158 or 164, while voice is carried over an audio channel 172 to this equipment.

A remote control unit (not shown) is preferably used to receive user inputs and responses to audio or displayed information and to pass these inputs to the internal analog telephony circuitry 134 for processing and, as needed, for transmissions to a PSTN 102 element or to a server connected over the PSTN 102.

Some services, e.g. 110 or 112 or 116 via 106A may be able to use the broadband network for both forward and backward transmission channels. In accordance with the present invention, the presence of analog telephony circuitry 134 and/or external analog telephones 152 and CPEs 154 allows servers and service providers to use the PSTN 102 as a backchannel to transmit control settings, user inputs, and other responses to a video server 114 via the PSTN, while the broadband network 106 transports the video or high speed data content to the BCID 100. ADSI functionality provides a good means to set up user control of a service such as 114. However, standard analog telephony signalling, such as signals from a DTMF keypad (not shown) associated with internal analog telephony circuitry 134 of the BCID could also be used to control interactive video 114 or data services (not shown, but connected like 114). To set up such a PSTN backchannel, a PSTN address of a server 114 could be dialed by BCID 100 in response to an ADSI soft key command. Alternatively, a server number could be stored in storage 142 and sent to an autodialer (not shown), which forms part of the analog telephony circuitry 134.

Over the PSTN connection 102 and 104 to the smart phone 154 or TV screen 158 or 164 via the BCID 100, the server 114 displays a menu of available videos or databases to the user. The user makes a selection which is transmitted through the PSTN 102 to the server 114. The server selects the desired information and transmits it via the broadband connection 106 to the BCID 100 for user viewing on any of the video or data terminals 158, 164, 160, or 162. The user can disconnect the PSTN call to the server 114 if no more selections are to be made, or remain connected via the PSTN for more choices.

In accordance with the present invention, NTDC 130 may be programmed dynamically via a variant of the broadband network download capability previously discussed, with trigger selection criteria and trigger functionality beyond basic AIN trigger capabilities. In this way, BCID 100 permits services that would require special, AIN-like call processing, even though they may not presently be technically or economically feasible via the PSTN.

To provide this AIN-like call processing, an AIN service node, such as SCP 116 can be programmed with the complementary functionality to perform the requested service. In this embodiment, BCID 100, once triggered by some network or user event, suspends its PSTN call processing and generates an AIN-like query message to SCP 116 over the broadband network 106 via 132 and 108. SCP 116 executes the desired call processing, in response to the query message, and sends the resulting call instructions either back to BCID 100 over the broadband network 106 or to an appropriate PSTN switch to complete the service function. For example, the SCP 116 might send back via the broadband network 106 a request for more information from the user. The user would enter the information via, e.g., remote controller keypad (not shown), and the response would be sent back to the SCP 116 via the broadband network 106.

Some examples of services that might be more easily implemented via the BCID 100 than the PSTN 102 are three-way call setup in response to a more reliable user input than an analog phone hook-flash, residential call transfer service, automatic initiation of a call to a preselected call party upon termination of a call in progress, or special features that activate upon detection of a busy or a no answer event. Triggers that have been defined, but that might not be deployed in the PSTN 102 for many years, if ever, can, with the present invention, be implemented by the NTDC 130 functionality at the interface to the PSTN access loop 104.

Outgoing PSTN 102 calls can be subjected to special processing by the SCP 116 before being offered to PSTN 102 and incoming calls can be subjected to special processing after being offered to the BCID 100 by the PSTN 102.

While there has been illustrated and described what are at present considered to be preferred embodiments and methods of the present invention, it will be understood by those skilled in the art that various changes and modifications may be made, and equivalents may be substituted for elements thereof without departing from the true scope of the invention.

For example, although the elements within BCID 100 shown in FIG. 2 are shown and described as being electronic circuitry, in accordance with the invention, these elements may, instead, comprise software applications or microcode or a combination of software or microcode and electronic circuitry to execute the disclosed functionality.

In addition, many modifications may be made to adapt a particular element, technique or implementation to the teachings of the present invention without departing from the central scope of the invention. Therefore, it is intended that this invention not be limited to the particular embodiments and methods disclosed herein, but that the invention include all embodiments falling within the scope of the appended claims.

We claim:

1. An interface device for connection to a customer premises equipment ("CPE") having a screen-phone device, and separate from a telephone network and separate from a broadband network, the interface device comprising:

first channel means for communicating telephony information between the CPE and the telephone network;

second channel means, separate from the first channel means, for communicating broadband information between the CPE and the broadband network;

means for routing the telephony information to the CPE via the interface device; and routing control means for routing programming information to the CPE in response to predetermined signals from the broadband network;

wherein the routing control means includes an analog display services interface ("ADSI") standard on-hook alerting ("AOHA") circuitry to alert the CPE to go off-hook without ringing the CPE; and wherein the broadband information includes programming information for the CPE.

2. The device of claim 1, further comprising storage means in the interface device to store the programming information until the CPE is ready to receive the programming information.

3. An interface device for video or data display devices for controlling broadband information delivery, comprising:

input/output ports for connecting the interface device to one or more video or data display devices;

first channel means for communicating with a telephone network;

second channel means for communicating with a broadband network;

means for generating control signals and sending the control signals to a broadband information provider via the telephone network;

means for receiving and processing the broadband information received via the broadband network; and routing means including an ADSI standard on-hook alerting circuitry for alerting the video or data display devices to go off-hook without ringing the video or data display devices.

4. A system for delivering broadband information to a remote device, comprising:

a telephone network;

a broadband network;

a broadband information provider connected to the telephone network and the broadband network; and an interface device connected to the remote device, the telephone network and the broadband network via separate connections, the interface device including means to transmit control signals from the remote device to the broadband information provider via the telephone network, and means to deliver broadband information from the broadband information provider to the remote device via the broadband network, including analog display services interface ("ADSI") standard on-hook alerting ("AOHA") circuitry to alert the remote device to go off-hook without ringing the remote device.

5. The system according to claim 4, wherein said remote device includes a display device.

6. A method of providing information to a customer premises equipment ("CPE"), comprising the steps of:

sending programming information to the CPE via a broadband network;

storing the programming information at an interface device, connected to the CPE which is separate from the broadband network, determining whether the CPE is idle;

requesting the CPE to go off-hook at times when the CPE is idle; and routing the programming information to the CPE after the CPE goes off-hook.

7. A method of controlling the delivery of broadband information to a remote device, comprising the steps of:

receiving from a broadband information provider, at an interface device associated with the remote device, a first set of control signals for controlling broadband information being delivered to the remote device;

routing a second set of control signals from the interface device to the broadband information provider via a telephone communication link through a telephone network; and delivering broadband information to the interface device via a broadband communication link through a broadband network in response to the second set of control signals, including the substeps of sending programming information from a broadband information provider to the remote device via the broadband network, storing the programming information at an interface device, connected to the remote device which is separate from the broadband network, and routing the programming information to the remote device by alerting the remote device to go off-hook without ringing the remote device.

* * * * *